United States Patent
Nelson et al.

(10) Patent No.: US 11,718,876 B2
(45) Date of Patent: *Aug. 8, 2023

(54) COMPOSITIONS AND METHODS FOR DETECTING ALLOGENEIC MATTER IN A SUBJECT

(71) Applicant: Fred Hutchinson Cancer Center, Seattle, WA (US)

(72) Inventors: J. Lee Nelson, Seattle, WA (US); Nathalie C. Lambert, Marseilles (FR); Vijayakrishna K. Gadi, Seattle, WA (US); Zhen Yan, Irving, TX (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,135

(22) Filed: Jun. 17, 2021

(65) Prior Publication Data

US 2021/0310068 A1 Oct. 7, 2021

Related U.S. Application Data

(63) Continuation of application No. 16/795,371, filed on Feb. 19, 2020, now Pat. No. 11,060,142, which is a continuation of application No. 14/382,105, filed as application No. PCT/US2013/028733 on Mar. 1, 2013, now Pat. No. 10,604,805.

(60) Provisional application No. 61/605,680, filed on Mar. 1, 2012.

(51) Int. Cl.
*C12Q 1/6881* (2018.01)
*C12Q 1/6883* (2018.01)

(52) U.S. Cl.
CPC ........ *C12Q 1/6881* (2013.01); *C12Q 1/6883* (2013.01); *C12Q 2600/156* (2013.01); *C12Q 2600/158* (2013.01)

(58) Field of Classification Search
CPC .................................................. C12Q 1/6881
See application file for complete search history.

(56) References Cited

U.S. PATENT DOCUMENTS

| 10,604,805 B2 | 3/2020 | Nelson et al. |
| 2020/0181701 A1 | 6/2020 | Nelson et al. |
| 2020/0181702 A1 | 6/2020 | Nelson et al. |

FOREIGN PATENT DOCUMENTS

| WO | 99/47706 A1 | 9/1999 |
| WO | 2005/000087 A2 | 1/2005 |

OTHER PUBLICATIONS

Adams et al., "Male DNA in female donor apheresis and CD34-enriched products," *Blood* 102(10):3845-3847, 2003.
Adams et al., "Microchimerism—An Investigative Frontier in Autoimmunity and Transplantation," *JAMA* 291(9):1127-1131, 2004.
Bonetta, "Prime time for real-time PCR," *Nature Methods* 2(4):305-312, 2005.

(Continued)

*Primary Examiner* — Diana B Johannsen
(74) *Attorney, Agent, or Firm* — Seed IP Law Group LLP

(57) ABSTRACT

The present disclosure provides a panel of nucleic acid molecule primers specific for HLA-specific alleles and other genetic polymorphisms, which are useful for quantitatively amplifying these markers to detect, diagnose, and monitor individuals who have or are at risk of certain disease conditions, such as autoimmune disease, proliferative disease, infectious disease, allograft rejection, or pregnancy-related pathologies.

19 Claims, 2 Drawing Sheets

Specification includes a Sequence Listing.

(56) References Cited

OTHER PUBLICATIONS

Evans et al., "Long-Term Fetal Microchimerism in Peripheral Blood Mononuclear Cell Subsets in Healthy Women and Women With Scleroderma," *Blood* 93(6):2033-2037, 1999.
Gadi, "Fetal microchimerism in breast from women with and without breast cancer," *Breast Cancer Res. Treat.* 121:241-244, 2010.
Gadi, "Fetal microchimerism and cancer," *Cancer Letters* 276:8-13, 2009.
Gadi et al., "Soluble Donor DNA Concentrations in Recipient Serum Correlate with Pancreas-Kidney Rejection," *Clinical Chemistry* 52(3):379-382, 2006.
Gadi et al., "Case-Control Study of Fetal Microchimerism and Breast Cancer," *PLoS One* 3(3):e1706, 2008. (5 pages).
Gadi et al., "Soluble Donor DNA and Islet Injury After Transplantation," *Transplantation* 92(5):607-611, 2011.
Gammill et al., "Effect of parity on fetal and maternal microchimerism: interaction of grafts within a host?," *Blood* 116(15):2706-2712, 2010.
Gamill et al., "Naturally acquired microchimerism," *Int. J. Dev. Biol.* 54(2-3):531-543, 2010.
Heid et al., "Real Time Quantitative PCR," *Genome Research* 6:986-994, 1996.
Lambert et al., "Quantification of Maternal Microchimerism by HLA-Specific Real-Time Polymerase Chain Reaction," *Arthritis & Rheumatism* 50(3):906-914, 2004.
Lee et al., "Survival of Donor Leukocyte Subpopulations in Immunocompetent Transfusion Recipients: Frequent Long-Term Microchimerism in Severe Trauma Patients," *Blood* 93(9):3127-3139, 1999.
Lo et al., "Quantitative Analysis of Fetal DNA in Maternal Plasma and Serum: Implications for Noninvasive Prenatal Diagnosis," *Am. J. Hum. Genet.* 62:768-775, 1998.
Loubière et al., "Maternal microchimerism in healthy adults in lymphocytes, monocyte/macrophages and NK cells," *Laboratory Investigation* 86:1185-1192, 2006.
Maloney et al., "Microchimerism of maternal origin persists into adult life," *J. Clin. Invest.* 104(1):41-47, 1999.
Marsh et al., "Nomenclature for factors of the HLA system, 2010," *Tissue Antigens* 75:291-455, 2010.
Nelson, "The Otherness of Self: Microchimerism in Health and Disease," *Trends Immunol.* 33(8):421-427, 2012.
Nelson et al., "Microchimerism and HLA-compatible relationships of pregnancy in scleroderma," *The Lancet* 351:559-562, 1998.
Nelson et al., "Maternal microchimerism in peripheral blood in type 1 diabetes and pancreatic islet $\beta$ cell microchimerism," *PNAS* 104(5):1637-1642, 2007.
"Procedures and Recommendations for Quantitative PCR," Plant-Microbe Genomics Facility, The Ohio State University, Columbus, OH, version 1.2, pp. 1-7, 2003.
Stevens et al., "Myocardial-tissue-specific phenotype of maternal microchimerism in neonatal lupus congenital heart block," *The Lancet* 362:1617-1623, 2003.
Stevens et al., "Maternal and sibling microchimerism in twins and triplets discordant for neonatal lupus syndrome-congenital heart block," *Rheumatology* 44:187-191, 2005.
Tyagi et al., "Molecular Beacons: Probes that Fluoresce upon Hybridization" *Nature Biotechnology* 14:303-308, 1996.
Yan et al., "Acquisition of the Rheumatoid Arthritis HLA Shared Epitope Through Microchimerism," *Arthritis Rheum.* 63(3):640-644, 2011.
Yan et al., "Prospective Study of Fetal DNA in Serum and Disease Activity During Pregnancy in Women With Inflammatory Arthritis," *Arthritis & Rheumatism* 54(7):2069-2073, 2006.
Kanaan et al., "Immunogenicity of a rheumatoid arthritis protective sequence when acquired through microchimerism," *PNAS* 116(39): 19600-19608, Sep. 24, 2019.

SEQUENCE LISTING

<160> NUMBER OF SEQ ID NOS: 89

<210> SEQ ID NO 1
<211> LENGTH: 18
<212> TYPE: DNA
<213> ORGANISM: Artificial Sequence
<220> FEATURE:
<223> OTHER INFORMATION: forward primer

<400> SEQUENCE: 1
ccgcgggtat gaccagga                                                  18

<210> SEQ ID NO 2
<211> LENGTH: 19
<212> TYPE: DNA
<213> ORGANISM: Artificial Sequence
<220> FEATURE:
<223> OTHER INFORMATION: reverse  primer

<400> SEQUENCE: 2
tccaggtatc tgcggagcg                                                 19

<210> SEQ ID NO 3
<211> LENGTH: 22
<212> TYPE: DNA
<213> ORGANISM: Artificial Sequence
<220> FEATURE:
<223> OTHER INFORMATION: Probe sequence

<400> SEQUENCE: 3
cggctcagat cacccagcgc aa                                             22

<210> SEQ ID NO 4
<211> LENGTH: 25
<212> TYPE: DNA

```
<213> ORGANISM: Artificial Sequence
<220> FEATURE:
<223> OTHER INFORMATION: forward primer

<400> SEQUENCE: 4
cacgtttctt gtggcagctt aagtt                                    25

<210> SEQ ID NO 5
<211> LENGTH: 17
<212> TYPE: DNA
<213> ORGANISM: Artificial Sequence
<220> FEATURE:
<223> OTHER INFORMATION: reverse primer

<400> SEQUENCE: 5
gctgtcgaag cgcacgg                                             17

<210> SEQ ID NO 6
<211> LENGTH: 34
<212> TYPE: DNA
<213> ORGANISM: Artificial Sequence
<220> FEATURE:
<223> OTHER INFORMATION: Probe sequence

<400> SEQUENCE: 6
tcctcttggt tatagatgca tctttccagc aacc                          34

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
cgtttcctgt ggcagcctaa                                          20

<210> SEQ ID NO 8
<211> LENGTH: 21
<212> TYPE: DNA
<213> ORGANISM: Artificial Sequence
<220> FEATURE:
<223> OTHER INFORMATION: reverse primer

<400> SEQUENCE: 8
gcacggactc ctcctggtta t                                        21

<210> SEQ ID NO 9
<211> LENGTH: 28
<212> TYPE: DNA
<213> ORGANISM: Artificial Sequence
<220> FEATURE:
<223> OTHER INFORMATION: Probe sequence

<400> SEQUENCE: 9
cgtcccattg aagaaatgac actccctc                                 28

<210> SEQ ID NO 10
<211> LENGTH: 26
<212> TYPE: DNA
<213> ORGANISM: Artificial Sequence
<220> FEATURE:
<223> OTHER INFORMATION: forward primer

<400> SEQUENCE: 10
ccacgtttct tggagtactc tacgtc                                   26
```

<210> SEQ ID NO 11
<211> LENGTH: 21
<212> TYPE: DNA
<213> ORGANISM: Artificial Sequence
<220> FEATURE:
<223> OTHER INFORMATION: reverse primer

<400> SEQUENCE: 11
tgcagtagtt gtccacccga c                                              21

<210> SEQ ID NO 12
<211> LENGTH: 34
<212> TYPE: DNA
<213> ORGANISM: Artificial Sequence
<220> FEATURE:
<223> OTHER INFORMATION: Probe sequence

<400> SEQUENCE: 12
ttctcctcct ggttatggaa gtatctgtcc aggt                                34

<210> SEQ ID NO 13
<211> LENGTH: 23
<212> TYPE: DNA
<213> ORGANISM: Artificial Sequence
<220> FEATURE:
<223> OTHER INFORMATION: forward primer

<400> SEQUENCE: 13
cgtttcttgg agcaggttaa aca                                            23

<210> SEQ ID NO 14
<211> LENGTH: 20
<212> TYPE: DNA
<213> ORGANISM: Artificial Sequence
<220> FEATURE:
<223> OTHER INFORMATION: reverse primer

<400> SEQUENCE: 14
cgcacgtact cctcttggtg                                                20

<210> SEQ ID NO 15
<211> LENGTH: 21
<212> TYPE: DNA
<213> ORGANISM: Artificial Sequence
<220> FEATURE:
<223> OTHER INFORMATION: Probe sequence

<400> SEQUENCE: 15
cacccgctcc gtcccgttga a                                              21

<210> SEQ ID NO 16
<211> LENGTH: 23
<212> TYPE: DNA
<213> ORGANISM: Artificial Sequence
<220> FEATURE:
<223> OTHER INFORMATION: forward primer

<400> SEQUENCE: 16
cgtttcctgt ggcagggtaa gta                                            23

<210> SEQ ID NO 17
<211> LENGTH: 22
<212> TYPE: DNA
<213> ORGANISM: Artificial Sequence
<220> FEATURE:

```
<223> OTHER INFORMATION: reverse primer

<400> SEQUENCE: 17
ccccgtagtt gtgtctgcac ac                                              22

<210> SEQ ID NO 18
<211> LENGTH: 28
<212> TYPE: DNA
<213> ORGANISM: Artificial Sequence
<220> FEATURE:
<223> OTHER INFORMATION: Probe sequence

<400> SEQUENCE: 18
aagtgtcatt tcttcaacgg gacggagc                                        28

<210> SEQ ID NO 19
<211> LENGTH: 24
<212> TYPE: DNA
<213> ORGANISM: Artificial Sequence
<220> FEATURE:
<223> OTHER INFORMATION: forward primer

<400> SEQUENCE: 19
acgtttcttg gagtactcta cggg                                            24

<210> SEQ ID NO 20
<211> LENGTH: 22
<212> TYPE: DNA
<213> ORGANISM: Artificial Sequence
<220> FEATURE:
<223> OTHER INFORMATION: reverse primer

<400> SEQUENCE: 20
gtctgcagta ggtgtccacc ag                                              22

<210> SEQ ID NO 21
<211> LENGTH: 32
<212> TYPE: DNA
<213> ORGANISM: Artificial Sequence
<220> FEATURE:
<223> OTHER INFORMATION: Probe sequence

<400> SEQUENCE: 21
tataaccaag aggagtacgt gcgcttcgac ag                                   32

<210> SEQ ID NO 22
<211> LENGTH: 20
<212> TYPE: DNA
<213> ORGANISM: Artificial Sequence
<220> FEATURE:
<223> OTHER INFORMATION: forward primer

<400> SEQUENCE: 22
gcacgtttct tgaagcagga                                                 20

<210> SEQ ID NO 23
<211> LENGTH: 22
<212> TYPE: DNA
<213> ORGANISM: Artificial Sequence
<220> FEATURE:
<223> OTHER INFORMATION: reverse primer

<400> SEQUENCE: 23
ccccgtagtt gtgtctgcac ac                                              22
```

```
<210> SEQ ID NO 24
<211> LENGTH: 34
<212> TYPE: DNA
<213> ORGANISM: Artificial Sequence
<220> FEATURE:
<223> OTHER INFORMATION: Probe sequence

<400> SEQUENCE: 24
ttctcctctt ggttatagat gcctctgtgc agat                                 34

<210> SEQ ID NO 25
<211> LENGTH: 18
<212> TYPE: DNA
<213> ORGANISM: Artificial Sequence
<220> FEATURE:
<223> OTHER INFORMATION: forward primer

<400> SEQUENCE: 25
ggttgctgga aagacgcg                                                   18

<210> SEQ ID NO 26
<211> LENGTH: 15
<212> TYPE: DNA
<213> ORGANISM: Artificial Sequence
<220> FEATURE:
<223> OTHER INFORMATION: reverse primer

<400> SEQUENCE: 26
gtgtccaccg cggca                                                      15

<210> SEQ ID NO 27
<211> LENGTH: 23
<212> TYPE: DNA
<213> ORGANISM: Artificial Sequence
<220> FEATURE:
<223> OTHER INFORMATION: Probe sequence

<400> SEQUENCE: 27
agtacgcgcg ctacgacagc gac                                             23

<210> SEQ ID NO 28
<211> LENGTH: 19
<212> TYPE: DNA
<213> ORGANISM: Artificial Sequence
<220> FEATURE:
<223> OTHER INFORMATION: forward primer

<400> SEQUENCE: 28
cggttgctgg aaagaagcg                                                  19

<210> SEQ ID NO 29
<211> LENGTH: 16
<212> TYPE: DNA
<213> ORGANISM: Artificial Sequence
<220> FEATURE:
<223> OTHER INFORMATION: reverse primer

<400> SEQUENCE: 29
ggtgtccacc gcggaa                                                     16

<210> SEQ ID NO 30
<211> LENGTH: 23
<212> TYPE: DNA
<213> ORGANISM: Artificial Sequence
<220> FEATURE:
<223> OTHER INFORMATION: Probe sequence
```

```
<400> SEQUENCE: 30
agtacgcgcg ctacgacagc gac                                          23

<210> SEQ ID NO 31
<211> LENGTH: 16
<212> TYPE: DNA
<213> ORGANISM: Artificial Sequence
<220> FEATURE:
<223> OTHER INFORMATION: forward primer

<400> SEQUENCE: 31
cggcctgctg cggaac                                                  16

<210> SEQ ID NO 32
<211> LENGTH: 22
<212> TYPE: DNA
<213> ORGANISM: Artificial Sequence
<220> FEATURE:
<223> OTHER INFORMATION: reverse primer

<400> SEQUENCE: 32
aaccccgtag ttgtgtctgc aa                                           22

<210> SEQ ID NO 33
<211> LENGTH: 20
<212> TYPE: DNA
<213> ORGANISM: Artificial Sequence
<220> FEATURE:
<223> OTHER INFORMATION: Probe sequence

<400> SEQUENCE: 33
ccgcctccgc tccaggaggt                                              20

<210> SEQ ID NO 34
<211> LENGTH: 25
<212> TYPE: DNA
<213> ORGANISM: Artificial Sequence
<220> FEATURE:
<223> OTHER INFORMATION: forward primer

<400> SEQUENCE: 34
caggctaagt gtgagtgtca tttcc                                        25

<210> SEQ ID NO 35
<211> LENGTH: 20
<212> TYPE: DNA
<213> ORGANISM: Artificial Sequence
<220> FEATURE:
<223> OTHER INFORMATION: reverse primer

<400> SEQUENCE: 35
cctggtactc ccccaggtca                                              20

<210> SEQ ID NO 36
<211> LENGTH: 29
<212> TYPE: DNA
<213> ORGANISM: Artificial Sequence
<220> FEATURE:
<223> OTHER INFORMATION: Probe sequence

<400> SEQUENCE: 36
tatctgatca ggttccacac tcgctccgt                                    29

<210> SEQ ID NO 37
<211> LENGTH: 21
```

<212> TYPE: DNA
<213> ORGANISM: Artificial Sequence
<220> FEATURE:
<223> OTHER INFORMATION: forward primer

<400> SEQUENCE: 37
cctggagagg aaggagactg c                                           21

<210> SEQ ID NO 38
<211> LENGTH: 21
<212> TYPE: DNA
<213> ORGANISM: Artificial Sequence
<220> FEATURE:
<223> OTHER INFORMATION: reverse primer

<400> SEQUENCE: 38
agccatgttt ctcagtgcac c                                           21

<210> SEQ ID NO 39
<211> LENGTH: 28
<212> TYPE: DNA
<213> ORGANISM: Artificial Sequence
<220> FEATURE:
<223> OTHER INFORMATION: Probe sequence

<400> SEQUENCE: 39
acctccaaat ttgctgaact caggccac                                    28

<210> SEQ ID NO 40
<211> LENGTH: 26
<212> TYPE: DNA
<213> ORGANISM: Artificial Sequence
<220> FEATURE:
<223> OTHER INFORMATION: forward primer

<400> SEQUENCE: 40
aatttgatgg agacgaggag ttctat                                      26

<210> SEQ ID NO 41
<211> LENGTH: 20
<212> TYPE: DNA
<213> ORGANISM: Artificial Sequence
<220> FEATURE:
<223> OTHER INFORMATION: reverse primer

<400> SEQUENCE: 41
gcaaattgcg ggtcaaatct                                             20

<210> SEQ ID NO 42
<211> LENGTH: 25
<212> TYPE: DNA
<213> ORGANISM: Artificial Sequence
<220> FEATURE:
<223> OTHER INFORMATION: Probe sequence

<400> SEQUENCE: 42
atctgcggaa cagaggcaac tgcca                                       25

<210> SEQ ID NO 43
<211> LENGTH: 23
<212> TYPE: DNA
<213> ORGANISM: Artificial Sequence
<220> FEATURE:
<223> OTHER INFORMATION: forward primer

<400> SEQUENCE: 43
ttgcactgac aaacatcgct atc         23

<210> SEQ ID NO 44
<211> LENGTH: 21
<212> TYPE: DNA
<213> ORGANISM: Artificial Sequence
<220> FEATURE:
<223> OTHER INFORMATION: reverse primer

<400> SEQUENCE: 44
tggtagcagc ggtagagttg g         21

<210> SEQ ID NO 45
<211> LENGTH: 20
<212> TYPE: DNA
<213> ORGANISM: Artificial Sequence
<220> FEATURE:
<223> OTHER INFORMATION: Probe sequence

<400> SEQUENCE: 45
aacttgaaca gtctgattaa         20

<210> SEQ ID NO 46
<211> LENGTH: 21
<212> TYPE: DNA
<213> ORGANISM: Artificial Sequence
<220> FEATURE:
<223> OTHER INFORMATION: forward primer

<400> SEQUENCE: 46
cgtgcgtctt gtgagcagaa g         21

<210> SEQ ID NO 47
<211> LENGTH: 17
<212> TYPE: DNA
<213> ORGANISM: Artificial Sequence
<220> FEATURE:
<223> OTHER INFORMATION: reverse primer

<400> SEQUENCE: 47
gtactcggcg gcaggca         17

<210> SEQ ID NO 48
<211> LENGTH: 21
<212> TYPE: DNA
<213> ORGANISM: Artificial Sequence
<220> FEATURE:
<223> OTHER INFORMATION: probe sequence

<400> SEQUENCE: 48
agcgtcaccg cccggaactc c         21

<210> SEQ ID NO 49
<211> LENGTH: 16
<212> TYPE: DNA
<213> ORGANISM: Artificial Sequence
<220> FEATURE:
<223> OTHER INFORMATION: forward primer

<400> SEQUENCE: 49
cggagcgcgt gcgtta         16

<210> SEQ ID NO 50
<211> LENGTH: 18
<212> TYPE: DNA
<213> ORGANISM: Artificial Sequence

```
<220> FEATURE:
<223> OTHER INFORMATION: reverse primer

<400> SEQUENCE: 50
cgtgcggagc tccaactg                                                 18

<210> SEQ ID NO 51
<211> LENGTH: 30
<212> TYPE: DNA
<213> ORGANISM: Artificial Sequence
<220> FEATURE:
<223> OTHER INFORMATION: probe sequence

<400> SEQUENCE: 51
aggacttcct tctggctgtt ccagtactcg                                    30

<210> SEQ ID NO 52
<211> LENGTH: 21
<212> TYPE: DNA
<213> ORGANISM: Artificial Sequence
<220> FEATURE:
<223> OTHER INFORMATION: forward primer

<400> SEQUENCE: 52
tgctacttca ccaacgggaa c                                             21

<210> SEQ ID NO 53
<211> LENGTH: 22
<212> TYPE: DNA
<213> ORGANISM: Artificial Sequence
<220> FEATURE:
<223> OTHER INFORMATION: reverse primer

<400> SEQUENCE: 53
ctattccagt actcggcgtc aa                                            22

<210> SEQ ID NO 54
<211> LENGTH: 30
<212> TYPE: DNA
<213> ORGANISM: Artificial Sequence
<220> FEATURE:
<223> OTHER INFORMATION: probe sequence

<400> SEQUENCE: 54
tcggttatag atgtatctgg tcacaccccg                                    30

<210> SEQ ID NO 55
<211> LENGTH: 18
<212> TYPE: DNA
<213> ORGANISM: Artificial Sequence
<220> FEATURE:
<223> OTHER INFORMATION: forward primer

<400> SEQUENCE: 55
gacgtggggg tgtaccgc                                                 18

<210> SEQ ID NO 56
<211> LENGTH: 17
<212> TYPE: DNA
<213> ORGANISM: Artificial Sequence
<220> FEATURE:
<223> OTHER INFORMATION: reverse primer

<400> SEQUENCE: 56
ctgcaagatc ccgcgga                                                  17
```

```
<210> SEQ ID NO 57
<211> LENGTH: 29
<212> TYPE: DNA
<213> ORGANISM: Artificial Sequence
<220> FEATURE:
<223> OTHER INFORMATION: probe sequence

<400> SEQUENCE: 57
ttccttctgg ctgttccagt actcggcat                                    29

<210> SEQ ID NO 58
<211> LENGTH: 20
<212> TYPE: DNA
<213> ORGANISM: Artificial Sequence
<220> FEATURE:
<223> OTHER INFORMATION: forward primer

<400> SEQUENCE: 58
ccagaaggac ctcctggagc                                              20

<210> SEQ ID NO 59
<211> LENGTH: 23
<212> TYPE: DNA
<213> ORGANISM: Artificial Sequence
<220> FEATURE:
<223> OTHER INFORMATION: reverse primer

<400> SEQUENCE: 59
gtgtctgcag taggtgtcca cag                                          23

<210> SEQ ID NO 60
<211> LENGTH: 12
<212> TYPE: DNA
<213> ORGANISM: Artificial Sequence
<220> FEATURE:
<223> OTHER INFORMATION: probe sequence

<400> SEQUENCE: 60
cggcccgcct ct                                                      12

<210> SEQ ID NO 61
<211> LENGTH: 20
<212> TYPE: DNA
<213> ORGANISM: Artificial Sequence
<220> FEATURE:
<223> OTHER INFORMATION: forward primer

<400> SEQUENCE: 61
ccagaaggac ctcctggagc                                              20

<210> SEQ ID NO 62
<211> LENGTH: 23
<212> TYPE: DNA
<213> ORGANISM: Artificial Sequence
<220> FEATURE:
<223> OTHER INFORMATION: reverse primer

<400> SEQUENCE: 62
gtgtctgcag taggtgtcca cag                                          23

<210> SEQ ID NO 63
<211> LENGTH: 12
<212> TYPE: DNA
<213> ORGANISM: Artificial Sequence
<220> FEATURE:
<223> OTHER INFORMATION: probe sequence
```

```
<400> SEQUENCE: 63
cggcccgctt ct                                                    12

<210> SEQ ID NO 64
<211> LENGTH: 20
<212> TYPE: DNA
<213> ORGANISM: Artificial Sequence
<220> FEATURE:
<223> OTHER INFORMATION: forward primer

<400> SEQUENCE: 64
ccagaaggac atcctggaag                                            20

<210> SEQ ID NO 65
<211> LENGTH: 23
<212> TYPE: DNA
<213> ORGANISM: Artificial Sequence
<220> FEATURE:
<223> OTHER INFORMATION: reverse primer

<400> SEQUENCE: 65
gtgtctgcag taggtgtcca cag                                        23

<210> SEQ ID NO 66
<211> LENGTH: 12
<212> TYPE: DNA
<213> ORGANISM: Artificial Sequence
<220> FEATURE:
<223> OTHER INFORMATION: probe sequence

<400> SEQUENCE: 66
cggcccgctc gt                                                    12

<210> SEQ ID NO 67
<211> LENGTH: 25
<212> TYPE: DNA
<213> ORGANISM: Artificial Sequence
<220> FEATURE:
<223> OTHER INFORMATION: probe sequence

<400> SEQUENCE: 67
ttggagtact ctacgggtga gtgtt                                      25

<210> SEQ ID NO 68
<211> LENGTH: 18
<212> TYPE: DNA
<213> ORGANISM: Artificial Sequence
<220> FEATURE:
<223> OTHER INFORMATION: probe sequence

<400> SEQUENCE: 68
gctgtcgaag cgcaggag                                              18

<210> SEQ ID NO 69
<211> LENGTH: 30
<212> TYPE: DNA
<213> ORGANISM: Artificial Sequence
<220> FEATURE:
<223> OTHER INFORMATION: probe sequence

<400> SEQUENCE: 69
tgcggttact ggagagacac ttccataacc                                 30

<210> SEQ ID NO 70
```

```
<211> LENGTH: 18
<212> TYPE: DNA
<213> ORGANISM: Artificial Sequence
<220> FEATURE:
<223> OTHER INFORMATION: forward primer

<400> SEQUENCE: 70
ttccaggagg cccatgag                                                       18

<210> SEQ ID NO 71
<211> LENGTH: 22
<212> TYPE: DNA
<213> ORGANISM: Artificial Sequence
<220> FEATURE:
<223> OTHER INFORMATION: reverse primer

<400> SEQUENCE: 71
gggcatcagc ttctgcttta tg                                                  22

<210> SEQ ID NO 72
<211> LENGTH: 24
<212> TYPE: DNA
<213> ORGANISM: Artificial Sequence
<220> FEATURE:
<223> OTHER INFORMATION: probe sequence

<400> SEQUENCE: 72
aaggccaagg acttcccacc tgca                                                24

<210> SEQ ID NO 73
<211> LENGTH: 29
<212> TYPE: DNA
<213> ORGANISM: Artificial Sequence
<220> FEATURE:
<223> OTHER INFORMATION: forward primer

<400> SEQUENCE: 73
cctctctcca taaagaaaac tatgagaga                                           29

<210> SEQ ID NO 74
<211> LENGTH: 29
<212> TYPE: DNA
<213> ORGANISM: Artificial Sequence
<220> FEATURE:
<223> OTHER INFORMATION: reverse primer

<400> SEQUENCE: 74
gctttataga aaaggaaaag gagagtatg                                           29

<210> SEQ ID NO 75
<211> LENGTH: 18
<212> TYPE: DNA
<213> ORGANISM: Artificial Sequence
<220> FEATURE:
<223> OTHER INFORMATION: probe sequence

<400> SEQUENCE: 75
cttggttcat acccaccc                                                       18

<210> SEQ ID NO 76
<211> LENGTH: 29
<212> TYPE: DNA
<213> ORGANISM: Artificial Sequence
<220> FEATURE:
<223> OTHER INFORMATION: forward primer

<400> SEQUENCE: 76
```

-continued cctctctcca taaagaaaac tatgagaga                                    29

<210> SEQ ID NO 77
<211> LENGTH: 30
<212> TYPE: DNA
<213> ORGANISM: Artificial Sequence
<220> FEATURE:
<223> OTHER INFORMATION: reverse primer

<400> SEQUENCE: 77 ggatttttg tttctcgtta actaaatcag                                    30

<210> SEQ ID NO 78
<211> LENGTH: 17
<212> TYPE: DNA
<213> ORGANISM: Artificial Sequence
<220> FEATURE:
<223> OTHER INFORMATION: probe sequence

<400> SEQUENCE: 78
ccctctacct gtaattc                                                 17

<210> SEQ ID NO 79
<211> LENGTH: 21
<212> TYPE: DNA
<213> ORGANISM: Artificial Sequence
<220> FEATURE:
<223> OTHER INFORMATION: forward primer

<400> SEQUENCE: 79
cacctccacc acccatagag a                                            21

<210> SEQ ID NO 80
<211> LENGTH: 25
<212> TYPE: DNA
<213> ORGANISM: Artificial Sequence
<220> FEATURE:
<223> OTHER INFORMATION: reverse primer

<400> SEQUENCE: 80
cgcagagtac attgtgaggt tttag                                        25

<210> SEQ ID NO 81
<211> LENGTH: 24
<212> TYPE: DNA
<213> ORGANISM: Artificial Sequence
<220> FEATURE:
<223> OTHER INFORMATION: probe sequence

<400> SEQUENCE: 81
tcctggccca tgttcccaag ctct                                         24

<210> SEQ ID NO 82
<211> LENGTH: 23
<212> TYPE: DNA
<213> ORGANISM: Artificial Sequence
<220> FEATURE:
<223> OTHER INFORMATION: forward primer

<400> SEQUENCE: 82
ggttacggtg tcagaaaacc tga                                          23

<210> SEQ ID NO 83
<211> LENGTH: 24
<212> TYPE: DNA

```
<213> ORGANISM: Artificial Sequence
<220> FEATURE:
<223> OTHER INFORMATION: reverse primer

<400> SEQUENCE: 83
agttccagca aacacttgaa gatg                                              24

<210> SEQ ID NO 84
<211> LENGTH: 28
<212> TYPE: DNA
<213> ORGANISM: Artificial Sequence
<220> FEATURE:
<223> OTHER INFORMATION: probe sequence

<400> SEQUENCE: 84
tctccagcct ctgtgttaat gtgagccc                                          28

<210> SEQ ID NO 85
<211> LENGTH: 20
<212> TYPE: DNA
<213> ORGANISM: Artificial Sequence
<220> FEATURE:
<223> OTHER INFORMATION: inhibitor oligonucleotide

<400> SEQUENCE: 85
acatcctgga gcaggcgcgg                                                   20

<210> SEQ ID NO 86
<211> LENGTH: 27
<212> TYPE: DNA
<213> ORGANISM: Artificial Sequence
<220> FEATURE:
<223> OTHER INFORMATION: forward primer

<400> SEQUENCE: 86
cagaccacgt ttcttggagt actctac                                           27

<210> SEQ ID NO 87
<211> LENGTH: 24
<212> TYPE: DNA
<213> ORGANISM: Artificial Sequence
<220> FEATURE:
<223> OTHER INFORMATION: reverse primer

<400> SEQUENCE: 87
ccttctggct gttccagtac tcct                                              24

<210> SEQ ID NO 88
<211> LENGTH: 26
<212> TYPE: DNA
<213> ORGANISM: Artificial Sequence
<220> FEATURE:
<223> OTHER INFORMATION: probe sequence

<400> SEQUENCE: 88
cgctccgtcc cattgaagaa atgaca                                            26

<210> SEQ ID NO 89
<211> LENGTH: 5
<212> TYPE: PRT
<213> ORGANISM: Homo sapiens

<400> SEQUENCE: 89

Asp Glu Arg Ala Ala
1               5
```

COMPOSITIONS AND METHODS FOR DETECTING ALLOGENEIC MATTER IN A SUBJECT

STATEMENT OF GOVERNMENT INTERESTS

This invention was made with government support under A1041721, A1045659, AR048084, A1045952, and HL117737 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 411C2_SEQUENCE_LISTING_V2.txt. The text file is 16.5 KB, was created on Feb. 17, 2023.

BACKGROUND

1. Technical Field

The present disclosure relates to compositions and methods for quantitatively amplifying nucleic acid molecules from biological samples and, more particularly, to a panel of nucleic acid molecules useful for quantitative amplification of target markers for detecting, diagnosing, or monitoring individuals who have or are at risk of certain disease conditions, such as autoimmune disease, proliferative disease, infectious disease, allograft rejection, or pregnancy-related pathologies.

2. Description of Related Art

Individuals harbor small amounts of foreign cells or DNA, referred to as microchimerism ("Mc"). Acquisition of Mc occurs naturally during pregnancy through transplacental cell trafficking between mother and fetus, although Mc may be acquired through other sources (e.g., blood transfusion, organ transplantation). An adult woman may have acquired Mc from her own mother (maternal Mc, "MMc") while she herself was a fetus. This "graft," acquired during fetal immune system development, can remain in her system into adulthood (Maloney et al., *J. Clin. Invest.* 104:41, 1999; Lambert et al., *Arth. Rheu.* 50:906, 2004) and represents a pre-existing inhabitant as she experiences pregnancy herself During subsequent pregnancies, new fetal sources of microchimerism (fetal Mc, "FMc") can be acquired and also remain for years. The interactions of each of these grafts with the host, and with other pre-existing inhabitants, may be beneficial or detrimental to an individual.

Disease and Mc may have a functional connection since persistence of Mc has been shown to be associated both positively and negatively with certain disease states, such as autoimmune disease (Evans et al., *Blood* 93:2033, 1999; Yan et al., *Arth. Rheu.* 63:640, 2011), malignancy (Gadi, *Breast Cancer Res. Treat.* 121:241, 2010; Gadi et al., *PLoS ONE* 3:e1706, 2008), and transplant rejection (Gadi et al., *Clin. Chem.* 52:379, 2006; Gadi et al., *Transpl.* 92:607, 2011). In autoimmunity, higher detection rates and concentrations of Mc suggest a possible allo-autoimmune or auto-alloimmune functionality (Gammill and Nelson, *Int. J. Dev. Biol.* 54:531, 2010). In the case of malignancy, lower detection rates and concentrations of Mc in cancer cases suggest a possible graft-versus-tumor effect (Gadi, *Cancer Lett.* 276:8, 2009). In transplantation, the presence of Mc may serve as a biomarker for monitoring allograft survival (Gadi et al., 2006, 2011).

From the foregoing, a need is apparent for improved compositions and methods for sensitively and quantitatively identifying allogeneic cells, tissues, and nucleic acids resulting from medical conditions or interventions.

BRIEF SUMMARY

In one aspect, the present disclosure provides compositions comprising a forward nucleic acid molecule, a reverse nucleic acid molecule, and a probe nucleic acid molecule comprising a fluorophore and a quencher, wherein each individual composition is specific for HLA-B*44, HLA-DRB1*01, HLA-DRB1*15/16, HLA-DRB1*03, HLA-DRB1*04, HLA-DRB1*07, HLA-DRB1*08, HLA-DRB1*09, HLA-DRB1*10, HLA-DRB1*14, HLA-DRB4, HLA-DQA1*01, HLA-DQA1*03, HLA-DQA1*05, HLA-DQB1*02, HLA-DQB 1*03, HLA-DQB1*04, HLA-DQB 1*06, SE-HR, SE-LR, GSTT 1, AT3, or Tg, as set forth in Table 1, and wherein each nucleic acid molecule has a length ranging from about 10 nucleotides to about 35 nucleotides.

In another aspect, the present disclosure provides methods for quantitating microchimerism, monitoring allograft rejection, anti-malignancy effects, engraftment dominance, or the like, wherein the methods involve amplifying nucleic acid molecules of a target biological sample using one or more specific nucleic acid compositions listed in Table 1 and analyzing for the presence or absence of certain specific amplified markers in the target biological sample to monitor or assess microchimerism, monitoring allograft rejection, anti-malignancy effects, engraftment dominance, or the like.

DETAILED DESCRIPTION

Figure 1:
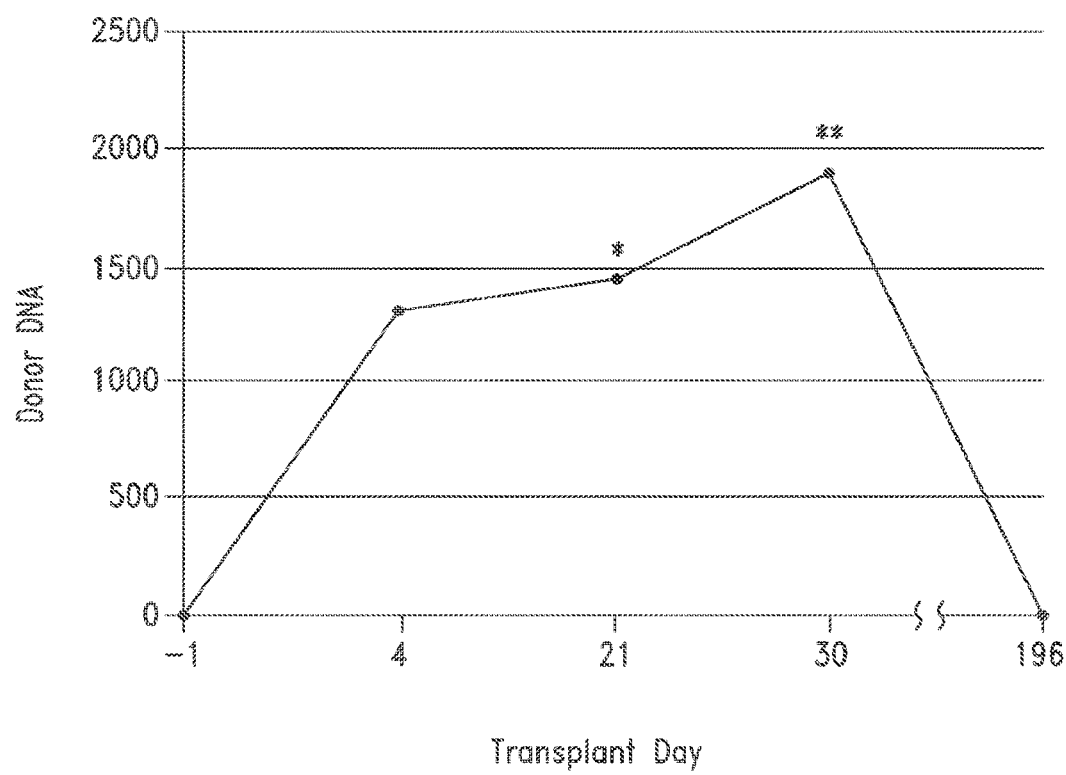
FIG. 1 shows a graph of the longitudinal assessment of donor DNA concentrations and acute transplant rejection (ACR). High concentrations of donor DNA (given in qEq/ 106 host genomes), as measured with the DQB1*06 nucleic acid molecule composition in Q-PCR, were detected in serum from a patient at points correlating with ACR in pancreas and kidney specimens (*) or pancreas alone (**). Day 196 was negative for ACR in the pancreas.

The present disclosure provides compositions of nucleic acid molecules for use in quantitatively detecting the presence of allogeneic material, such as cells or DNA, in a subject. Such compositions and methods can be useful in detecting microchimerism, transplant rejection, malignancy relapse, potential pathology associated with pregnancy, infectious disease, or the like. Exemplary compositions include a forward nucleic acid molecule, a reverse nucleic acid molecule, and a probe nucleic acid molecule comprising a fluorophore and a quencher, wherein each composition is specific for a particular HLA allele, for particular polymorphisms of an HLA allele, or for other genetic polymorphisms with different alleles or a null allele.

By way of background, some cells may (and often times do) traffic between a mother and fetus during pregnancy. Surprisingly, small numbers of these allogeneic cells can persist in their respective hosts decades later. Microchimerism (Mc) refers to an individual harboring a small number of cells, or DNA, derived from another individual. As noted above, the instant disclosure provides compositions and methods for examining a wide breadth of consequences of naturally-acquired Mc across all of human health (Adams and Nelson, *JAMA* 291:1127, 2004).

For example, Mc may have an effect on or have a role in autoimmune disease. In a first study of Mc, elevated levels of fetal Mc in blood were found in women with scleroderma compared to healthy women (Nelson et al., *Lancet* 351:559, 1998). Fetal Mc (FMc) has since been investigated in primary biliary cirrhosis, thyroiditis, Sjögren's syndrome, polymorphic eruption of pregnancy and rheumatoid arthritis. Maternal Mc (MMc) can be found in her adult progeny (Maloney et al., *J. Clin. Invest.* 104:41, 1999). MMc has been studied in neonatal lupus, systemic lupus and myositis. In neonatal lupus with heart block, maternal cells in the heart were cardiac myocytes (Stevens et al., *Lancet* 362:1617, 2003). Thus, microchimeric cells could be targets or alternatively could help repair damaged tissues. FMc may be beneficial during pregnancy in women with rheumatoid arthritis as elevated levels, assessed by Q-PCR, significantly correlated with pregnancy-induced amelioration of arthritis (Yan et al., *Arthritis Rheum.* 54:2069, 2006).

In cancer, hematopoietic cell transplantation (HCT) donor cells provide an advantage against recurrent leukemia and other malignancies. By analogy, FMc might be responsible for protection from breast cancer observed in women who have had prior pregnancies compared to those who have not. In other types of malignancies, anecdotal reports indicate that microchimeric cells may cause or result in malignancy.

For infectious disease, T lymphocytes are an important determinant of immune reactions between one's own cells and foreign cells. Human immunodeficiency virus (HIV) and acquired immunodeficiency syndrome (AIDS) are characterized by critical deficiencies in CD4+ T cells. MMc can be examined in HIV and AIDS by employing HLA and other genetic polymorphism specific Q-PCR to quantify MMc in men with HIV to correlate results progression as compared to non-progression to AIDS.

In the field of transplantation, iatrogenic chimerism can result. But, donor Mc may facilitate graft acceptance. Until recently, donor Mc was measured as male DNA in female recipients, but it is now clear that women commonly have male DNA from prior pregnancies. Thus, the application of specific Q-PCR assays of this disclosure provides a major step forward for these studies. In hematopoietic cell transplantation (HCT), graft-versus-host disease (GVHD) occurs more often if the donor is a woman with prior pregnancies. Female apheresis products were found to contain male Mc, consistent with the idea that fetal Mc contributes to GVHD (Adams et al., *Blood* 15:3845, 2003). In kidney, pancreas and islet transplantation embodiment, the panel of Q-PCR assays of the instant disclosure are useful for testing serial serum samples, which provides a non-invasive test for early rejection (see Example 1). The Q-PCR assays of the instant disclosure may also be used to monitor the fate of co-transplanted hematopoietic cells as it affects a kidney allograft from the same donor.

In the context of pregnancy, the compositions and methods of the instant disclosure are useful for identifying changes in the maternal carriage of fetal cells throughout the course of normal pregnancy (see Example 2). In certain embodiments, the tools and methods of the instant disclosure can be used to examine pathologic conditions associated with pregnancy (pre-eclampsia, early fetal loss, and abnormally genetic fetuses, as examples) and their association with deviations from normal pregnancy patterns.

Prior to setting forth this disclosure in more detail, it may be helpful to an understanding thereof to provide definitions of certain terms to be used herein. Additional definitions are set forth throughout this disclosure.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, "fluorophore" refers to a molecule that emits light of a certain wavelength after having first absorbed light of a specific, but shorter, wavelength, wherein the emission wavelength is always higher than the absorption wavelength.

As used herein, "quencher" refers to a molecule that accepts energy from a fluorophore in the form of light at a particular wavelength and dissipates this energy either in the form of heat (e.g., proximal quenching) or light of a higher wavelength than emitted from the fluorophore (e.g., FRET quenching). Quenchers generally have a quenching capacity throughout their absorption spectrum, but they perform best close to their absorption maximum. For example, Deep Dark Quencher II absorbs over a large range of the visible spectrum and, consequently, efficiently quenches most of the commonly used fluorophores, especially those emitting at higher wavelengths (like the Cy® dyes). Similarly, the Black Hole Quencher family covers a large range of wavelengths (over the entire visible spectrum and into the near-IR). In contrast, Deep Dark Quencher I and Eclipse® Dark Quencher effectively quench the lower wavelength dyes, such as FAM, but do not quench very effectively those dyes that emit at high wavelengths.

As used herein, "target nucleic acid molecules" and variants thereof refer to a plurality of nucleic acid molecules that may be found in certain biological samples but may be missing from others, depending on the genetic make-up of the subject and the extent of microchimerism present. Nucleic acid molecules include those from natural samples (e.g., a genome, RNA), or the target nucleic acid molecules may be synthetic samples (e.g., cDNA), recombinant samples, or a combination thereof.

As used herein, a "nucleic acid molecule primer" or "primer" and variants thereof refers to short nucleic acid sequences that a DNA polymerase can use to begin synthesizing a complementary DNA strand of the molecule bound by the primer. A primer sequence can vary in length from 5 nucleotides to about 50 nucleotides in length, from about 10 nucleotides to about 35 nucleotides, and preferably are about 15, 16, 17, 18, 19, 20, 21, 22, 23, 24, 25, 26, 27, 28, 29, 30, 31, 32, 33, 34, or 35 nucleotides in length. In certain embodiments, a nucleic acid molecule primer that is complementary to a target nucleic acid of interest can be used to initiate an amplification reaction, a sequencing reaction, or both.

For example, for quantitative PCR, the combination of an upstream or forward primer (5') and a downstream or reverse primer (3') complementary to a target sequence of interest (e.g., HLA-B, HLA-DRB) can be used to prime an amplification reaction to obtain the sequence of the nucleic acid molecule of interest. A "probe" oligonucleotide sequence is similar to a primer except that it will further contain a fluorophore molecule and a quencher molecule and hybridize to a target nucleic acid molecule of interest somewhere between the forward and reverse primer binding sites.

In the following description, certain specific details are set forth in order to provide a thorough understanding of various embodiments of this disclosure. However, upon reviewing this disclosure one skilled in the art will understand that the invention may be practiced without many of these details. In other instances, newly emerging amplification technologies, as well as well-known or widely available specific probe amplification methods and tools (e.g., Taqman® probes, Locked Nucleic Acid (LNA) probes, Molecular Beacon probes, Scorpions® primers, Hybridization probes, MGB probes, QuantiProbes, Resonsense probes, Light-up probes, HyBeacon® probes, LUX primers, Yin-yang probes, Amplifluor®), have not all been described in detail to avoid unnecessarily obscuring the descriptions of the embodiments of the present disclosure.

Various embodiments of the present disclosure are described for purposes of illustration, in the context of use with HLA-specific alleles and certain other genomic polymorphisms. But, as those skilled in the art will appreciate upon reviewing this disclosure, use with other target nucleic acid molecules may also be suitable.

In certain embodiments, the present disclosure provides methods for detecting, diagnosing, or monitoring the presence of allogeneic cells, tissues, or nucleic acid molecules that may be involved in or associated with a particular medical condition, such as autoimmune disease, neoplastic disorders, infectious disease, transplant rejection, and pathologies associated with pregnancy. In further embodiments, the methods of the instant disclosure are sensitive enough to detect one chimeric genome in $10^5$ host genomes or $10^6$ host genomes when amplifying specific target nucleic acid molecules in presence of many different nucleic acid molecules.

In further embodiments, the compositions and methods of this instant disclosure will be useful in detecting rare nucleic acid molecules or cells against a large background signal, such as when monitoring for Mc in autoimmune disease, infectious disease, malignancies, transplant subjects, pregnancy, or forensics. Additional embodiments may be used to quantify target nucleic acid molecules that may be indicative of response to therapy or may be useful in monitoring disease progression or recurrence. In yet other embodiments, these compositions and methods may be useful in detecting or monitoring target nucleic acid molecules after or during chemotherapy, autoimmune therapy, infectious disease therapy, or treatments of complications to pregnancy.

Representative nucleic acid molecule compositions of the present disclosure may be specific for HLA alleles, such as HLA-B*44, HLA-DRB1*01, HLA-DRB1*15/16, HLA-DRB1*03, HLA-DRB1*04, HLA-DRB1*07, HLA-DRB1*08, HLA-DRB1*09, HLA-DRB1*10, HLA-DRB1*14, HLA-DRB4, HLA-DQA1*01, HLA-DQA1*03, HLA-DQA1*05, HLA-DQB1*02, HLA-DQB1*03, HLA-DQB1*04, or HLA-DQB1*06 (see Table 1). Alternatively, nucleic acid molecule compositions of the present disclosure may be specific for other genetic polymorphisms, such as SE-HR, SE-LR, GSTT1, AT3, or Tg (see Table 1). In certain embodiments, each nucleic acid molecule has a length ranging from about 10 nucleotides to about 35 nucleotides.

Selecting nucleic acid molecule compositions of the present disclosure is not routine because many of the sequences tested did not work due to cross-reactivity with other genes. For example, the DRB1*11 specific primers and probes described in Example 1 did not work because multiple cross-reactivity did not allow for analysis of this marker. Alternative sequences for this marker also did not work. Similarly, DRB1*05 and DQB1*05 did not work, and a particular primer pair for DRB1*10 (see HLA-DRB1*10-2 SEQ ID NOS.:28 and 29 of Table 1) also did not work, as well as various other primers and probes (not shown) for the targets listed in Table 1.

The probe nucleic acid molecules of the compositions of the present disclosure are preferably dual labeled oligonucleotides that include a fluorophore (e.g., FAM, TET, HEX, Cy®3, Cy®3.5, Cy®5, Cy®5.5, TAMRA, Yakima Yellow®, ROX) and a quencher (e.g., Deep Dark Quencher I, Deep Dark Quencher II, DabCYL, Eclipse® Dark Quencher, Black Hole Quencher (BHQ-0, BHQ-1, BHQ-2, BHQ-3, TAMRA). For example, the instant disclosure provides HLA and other genetic polymorphism-specific quantitative PCR (Q-PCR) primers and probes for use in diagnostics, detection of medical conditions, or monitoring medical conditions.

An exemplary panel of primers and probes useful in the compositions and methods of the instant disclosure are provided in Table 1.

TABLE 1 qPCR Primers and Probes*

| Target | Forward (5'-3') | Reverse (3'-5') | Probe (5'-3') |
|---|---|---|---|
| HLA-B*44 | CCG CGG GTA TGA CCA GGA (SEQ ID NO.: 1) | TCC AGG TAT CTG CGG AGC G (SEQ ID NO.: 2) | CGG CTC AGA TCA CCC AGC GCA A (SEQ ID NO.: 3) |
| HLA-DRB1*01 | CAC GTT TCT TGT GGC AGC TTA AGT T (SEQ ID NO.: 4) | GCT GTC GAA GCG CAC GG (SEQ ID NO.: 5) | TC CTC TTG GTT ATA GAT GCA TCT TTC CAG CAA CC (SEQ ID NO.: 6) |
| HLA-DRB1*15/16 | CGT TTC CTG TGG CAG CCT AA (SEQ ID NO.: 7) | GCA CGG ACT CCT CCT GGT TAT (SEQ ID NO.: 8) | CGT CCC ATT GAA GAA ATG ACA CTC CCT C (SEQ ID NO.: 9) |

TABLE 1-continued qPCR Primers and Probes*

| Target | Forward (5'-3') | Reverse (3'-5') | Probe (5'-3') |
|---|---|---|---|
| HLA-DRB1*03 | CCA CGT TTC TTG GAG TAC TCT ACG TC (SEQ ID NO.: 10) | T GCA GTA GTT GTC CAC CCG AC (SEQ ID NO.: 11) | TT CTC CTC CTG GTT ATG AAA GTA TCT GTC CAG GT (SEQ ID NO.: 12) |
| HLA-DRB1*04 | CGT TTC TTG GAG CAG GTT AAA CA (SEQ ID NO.: 13) | CG CAC GTA CTC CTC TTG GTG (SEQ ID NO.: 14) | CAC CCG CTC CGT CCC GTT GAA (SEQ ID NO.: 15) |
| HLA-DRB1*07 | CGT TTC CTG TGG CAG GGT AAG TA (SEQ ID NO.: 16) | C CCC GTA GTT GTG TCT GCA CAC (SEQ ID NO.: 17) | AAG TGT CAT TTC TTC AAC GGG ACG GAG C (SEQ ID NO.: 18) |
| HLA-DRB1*08 | A CGT TTC TTG GAG TAC TCT ACG GG (SEQ ID NO.: 19) | G TCT GCA GTA GGT GTC CAC CAG (SEQ ID NO.: 20) | TAT AAC CAA GAG GAG TAC GTG CGC TTC GAC AG (SEQ ID NO.: 21) |
| HLA-DRB1*09 | G CAC GTT TCT TGA AGC AGG A (SEQ ID NO.: 22) | C CCC GTA GTT GTG TCT GCA CAC (SEQ ID NO.: 23) | T TCT CCT CTT GGT TAT AGA TGC CTC TGT GCA GAT (SEQ ID NO.: 24) |
| HLA-DRB1*10-1 | GGT TGC TGG AAA GAC GCG (SEQ ID NO.: 25) | GTG TCC ACC GCG GCA (SEQ ID NO.: 26) | AGT ACG CGC GCT ACG ACA GCG AC (SEQ ID NO.: 27) |
| HLA-DRB1*10-2¶ | CGG TTG CTG GAA AGA AGC G (SEQ ID NO.: 28) | GGT GTC CAC CGC GGA A (SEQ ID NO.: 29) | AGT ACG CGC GCT ACG ACA GCG AC (SEQ ID NO.: 27) |
| HLA-DRB1*14 | CGG CCT GCT GCG GAA C (SEQ ID NO.: 31) | AAC CCC GTA GTT GTG TCT GCA A (SEQ ID NO.: 32) | CCG CCT CCG CTC CAG GAG GT (SEQ ID NO.: 33) |
| HLA-DRB4*01 | CAG GCT AAG TGT GAG TGT CAT TTC C (SEQ ID NO.: 34) | CCT GGT ACT CCC CCA GGT CA (SEQ ID NO.: 35) | TA TCT GAT CAG GTT CCA CAC TCG CTC CGT (SEQ ID NO.: 36) |
| HLA-DQA1*01 | C CTG GAG AGG AAG GAG ACT GC (SEQ ID NO.: 37) | AGC CAT GTT TCT CAG TGC ACC (SEQ ID NO.: 38) | ACC TCC AAA TTT GCT GAA CTC AGG CCA C (SEQ ID NO.: 39) |
| HLA-DQA1*03 | AA TTT GAT GGA GAC GAG GAG TTC TAT (SEQ ID NO.: 40) | GC AAA TTG CGG GTC AAA TCT (SEQ ID NO.: 41) | A TCT GCG AAC AGG AGG CAA CTG CCA (SEQ ID NO.: 42) |
| HLA-DQA1*05 | TTG CAC TGA CAA ACA TCG CTA TC (SEQ ID NO.: 43) | TGG TAG CAG CGG TAG AGT TGG (SEQ ID NO.: 44) | AAC TTG AAC AGT CTG ATT AA (SEQ ID NO.: 45) |
| HLA-DQB* | C GTG CGT CTT GTG AGC AGA AG (SEQ ID NO.: 46) | GTA CTC GGC GGC AGG CA (SEQ ID NO.: 47) | AG CGT CAC CGC CCG GAA CTC C (SEQ ID NO.: 48) |
| HLA-DQB1*03 | CGG AGC GCG TGC GTT A (SEQ ID NO.: 49) | CGT GCG GAG CTC CAA CTG (SEQ ID NO.: 50) | AG GAC TTC CTT CTG GCT GTT CCA GTA CTC G (SEQ ID NO.: 51) |

TABLE 1-continued qPCR Primers and Probes*

| Target | Forward (5'-3') | Reverse (3'-5') | Probe (5'-3') |
|---|---|---|---|
| HLA-DQB1*04 | TGC TAC TTC ACC AAC GGG AAC (SEQ ID NO.: 52) | CTA TTC CAG TAC TCG GCG TCA A (SEQ ID NO.: 53) | TCG GTT ATA GAT GTA TCT GGT CAC ACC CCG (SEQ ID NO.: 54) |
| HLA-DQB1*06 | GAC GTG GGG GTG TAC CGC (SEQ ID NO.: 55) | CTG CAA GAT CCC GCG GA (SEQ ID NO.: 56) | TTC CTT CTG GCT GTT CCA GTA CTC GGC AT (SEQ ID NO.: 57) |
| SE-HR (QRRAA)† | CCA GAA GGA CCT CCT GGA GC (SEQ ID NO.: 58) | GTG TCT GCA GTA GGT GTC CAC AG (SEQ ID NO.: 59) | CGG CCC GCC TCT (SEQ ID NO.: 60) |
| SE-HR (QKRAA)† | CCA GAA GGA CCT CCT GGA GC (SEQ ID NO.: 61) | GTG TCT GCA GTA GGT GTC CAC AG (SEQ ID NO.: 62) | CGG CCC GCT TCT (SEQ ID NO.: 63) |
| SE-LR (DERAA) | CCA GAA GGA CAT CCT GGA AG (SEQ ID NO.: 64) | GTG TCT GCA GTA GGT GTC CAC AG (SEQ ID NO.: 65) | CGG CCC GCT CGT (SEQ ID NO.: 66) |
| GSTT1 | TTC CAG GAG GCC CAT GAG (SEQ ID NO.: 70) | GGG CAT CAG CTT CTG CTT TAT G (SEQ ID NO.: 71) | AAG GCC AAG GAC TTC CCA CCT GCA (SEQ ID NO.: 72) |
| AT3-S | CCT CTC TCC ATA AAG AAA ACT ATG AGA GA (SEQ ID NO.: 73) | GCT TTA TAG AAA AGG AAA AGG AGA GTA TG (SEQ ID NO.: 74) | CTT GGT TCA TAC CCA CCC (SEQ ID NO.: 75) |
| AT3-L | CCT CTC TCC ATA AAG AAA ACT ATG AGA GA (SEQ ID NO.: 76) | GGA TTT TTT GTT TCT CGT TAA CTA AAT CAG (SEQ ID NO.: 77) | CCC TCT ACC TGT AAT TC (SEQ ID NO.: 78) |
| Tg-I | CAC CTC CAC CAC CCA TAG AGA (SEQ ID NO.: 79) | CGC AGA GTA CAT TGT GAG GTT TTA G (SEQ ID NO.: 80) | TCC TGG CCC ATG TTC CCA AGC TCT (SEQ ID NO.: 81) |
| Tg-D | GGT TAC GGT GTC AGA AAA CCT GA (SEQ ID NO.: 82) | AGT TCC AGC AAA CAC TTG AAG ATG (SEQ ID NO.: 83) | TCT CCA GCC TCT GTG TTA ATG TGA GCC C (SEQ ID NO.: 84) |

*Nucleotides identified in bold and underline are an artificial nucleotide mismatch to the native sequence.
¶This particular pair of forward/reverse primers, named HLA-DRB1*10-2, did not work.
†The SE-HR (Shared Epitope-High Risk) qPCR reactions will also include an inhibitor oligonucleotide as follows: ACA TCC TGG AGC AGG CGC GG (SEQ ID NO.: 85).

In a test for MMc in a child, for example, a person of skill in the art may decide to target HLA-DRB1* as an approach to selecting one or more nucleic acid molecule compositions from Table 1. The initial step would be to conduct HLA-genotyping on the child, mother and father. For example, the HLA genotypes may be HLA-DRB1*01/HLA-DRB1*15 for the mother, HLA-DRB1*03/HLA-DRB1*14 for the father, and HLA-DRB1*01/HLA-DRB1*03 for the child. Examination of the HLA-genotyping indicates that the non-shared HLA allele of the mother as compared to the child is HLA-DRB1*03. So, DNA is extracted from the child and interrogated for MMc employing the appropriate HLA-specific Q-PCR assay from among the panel of assays listed in Table 1—in this case, one would use a composition of three nucleic acid molecules that includes SEQ ID NOS.:10, 11, and 12. In addition, an irrelevant HLA-specific Q-PCR assay can be included in testing the child as a negative control.

In certain embodiments, the instant disclosure provides a process for quantitating microchimerism, comprising: (a) amplifying nucleic acid molecules of a target biological sample using one or more specific nucleic acid compositions from Table 1; (b) amplifying nucleic acid molecules of a control biological sample using the one or more specific nucleic acid molecule compositions of step (a); (c) comparing the amount of amplified nucleic acid molecules with a reference to quantitate the specific nucleic acid molecule markers in the samples; wherein the presence of certain specific amplified markers in the target biological sample indicates the presence of microchimerism.

Umbilical cord blood and bone marrow transplants can be used to cure or slow the progression of many cancers originating in the bone marrow (e.g., leukemia, myeloma) or lymphatic system (e.g., lymphoma). In certain embodiments, nucleic acid molecule compositions and methods of the instant disclosure can be used to determine donor MMc to identify one or more donor cord blood or donor bone marrow that will provide the greatest anti-malignancy or anti-relapse potential.

For example, if the HLA-B* is being targeted, then HLA-genotyping would be conducted on the patient, the patient's mother, a first cord blood donor, the first cord blood donor's mother, a second cord blood donor, and the second cord blood donor's mother. The HLA genotypes may be HLA-B*08/HLA-B*15 for the patient, HLA-B*08/HLA-B*44 for the patient's mother, HLA-B*22/HLA-B*15 for the first cord blood donor, HLA-B*22/HLA-B*35 for the first cord blood donor's mother, HLA-B*08/HLA-B*13 for the second cord blood donor, and HLA-B*08/HLA-B*37 for the second cord blood donor's mother. Examination of the HLA-genotyping indicates that the first cord blood donor shares the patient's inherited paternal antigen (IPA), HLA-B*15; therefore, the first cord blood donor would provide the greatest anti-malignancy or anti-relapse potential. By way of illustration and not wishing to be bound by theory, the benefit for the patient to receive the first donor's cord blood would be due to effector T cells of the donor's mother that have previously been exposed to the same HLA molecule as the patient's IPA (i.e., HLA-B*15). In contrast, effector T cells of the mother donor for the second cord blood donor would have reactivity to HLA-B*13, which is not shared with the patient.

If, however, the mother does not have a unique HLA allele (i.e., the mother and child are HLA identical or the child is HLA homozygous) or a set nucleic acid molecules of the instant disclosure are not available, testing can be done on genetic polymorphisms found on other chromosomes. Exemplary nucleic acid molecule compositions from Table 1 include, for example, glutathione S-transferase 01 (GSTT1), anti-thrombin III long (AT3-L), anti-thrombin III short (AT3-S), thyroglobulin insertion (Tg-I) and thyroglobulin deletion (Tg-D). All nucleic acid molecule compositions have been validated for specificity using Q-PCR assays tested against an extensive panel of DNA derived from fully HLA characterized cell lines from the 13th International HLA Workshop (see www.ihwg.org; see also Marsh et al., *Tissue Antigens* 75:291, 2010).

In certain medical situations, patients may receive a double cord blood transplant. So in the previous example, although a patient may receive a double cord blood transplant, only one of the donors may provide a benefit. In certain embodiments, the nucleic acid molecule compositions and methods of the instant disclosure can be used to determine which plurality of donor cord blood or donor bone marrow would be best to combine. In a further embodiment, the nucleic acid molecule compositions and methods of the instant disclosure can be used to determine which donor cord blood or donor bone marrow from a pooled transplant would dominantly engraft.

For example, if the HLA-B* is again being targeted, then HLA-genotyping would be conducted on the patient, the patient's mother, a first cord blood donor, the first cord blood donor's mother, a second cord blood donor, and the second cord blood donor's mother. The HLA genotypes may be HLA-B*08/HLA-B*15 for the patient, HLA-B*08/HLA-B*44 for the patient's mother, HLA-B*22/HLA-B*12 for the first cord blood donor, HLA-B*22/HLA-B*35 for the first cord blood donor's mother, HLA-B*18/HLA-B*44 for the second cord blood donor, and HLA-B*18/HLA-B*37 for the second cord blood donor's mother. Examination of the HLA-genotyping indicates that the second cord blood donor shares the patient's non-inherited maternal antigen (NIMA), HLA-B*44; therefore, the second cord blood donor would provide the greatest potential for dominant engraftment—in this case, one would use a composition of three nucleic acid molecules that includes SEQ ID NOS.:1, 2, and 3.

In further embodiments, the instant disclosure provides a composition comprising nucleic acid molecules specific for HLA-DRB1*01, wherein the forward nucleic acid molecule comprises a sequence as set forth in SEQ ID NO.:4, the reverse nucleic acid molecule comprises a sequence as set forth in SEQ ID NO.:5, and the probe nucleic acid molecule comprises a sequence as set forth in SEQ ID NO.:6.

In further embodiments, the instant disclosure provides a composition comprising nucleic acid molecules specific for HLA-DRB1*15/16, wherein the forward nucleic acid molecule comprises a sequence as set forth in SEQ ID NO.:7, the reverse nucleic acid molecule comprises a sequence as set forth in SEQ ID NO.:8, and the probe nucleic acid molecule comprises a sequence as set forth in SEQ ID NO.:9.

In further embodiments, the instant disclosure provides a composition comprising nucleic acid molecules specific for HLA-DRB1*03, wherein the forward nucleic acid molecule comprises a sequence as set forth in SEQ ID NO.:10, the reverse nucleic acid molecule comprises a sequence as set forth in SEQ ID NO.:11, and the probe nucleic acid molecule comprises a sequence as set forth in SEQ ID NO.:12.

In further embodiments, the instant disclosure provides a composition comprising nucleic acid molecules specific for HLA-DRB1*07, wherein the forward nucleic acid molecule comprises a sequence as set forth in SEQ ID NO.:16, the reverse nucleic acid molecule comprises a sequence as set forth in SEQ ID NO.:17, and the probe nucleic acid molecule comprises a sequence as set forth in SEQ ID NO.:18.

In further embodiments, the instant disclosure provides a composition comprising nucleic acid molecules specific for HLA-DRB1*08, wherein the forward nucleic acid molecule comprises a sequence as set forth in SEQ ID NO.:19, the reverse nucleic acid molecule comprises a sequence as set forth in SEQ ID NO.:20, and the probe nucleic acid molecule comprises a sequence as set forth in SEQ ID NO.:21.

In further embodiments, the instant disclosure provides a composition comprising nucleic acid molecules specific for HLA-DRB1*09, wherein the forward nucleic acid molecule comprises a sequence as set forth in SEQ ID NO.:22, the reverse nucleic acid molecule comprises a sequence as set forth in SEQ ID NO.:23, and the probe nucleic acid molecule comprises a sequence as set forth in SEQ ID NO.:24.

In further embodiments, the instant disclosure provides a composition comprising nucleic acid molecules specific for HLA-DRB1*10, wherein (a) the forward nucleic acid molecule comprises a sequence as set forth in SEQ ID NO.:25, the reverse nucleic acid molecule comprises a sequence as set forth in SEQ ID NO.:26, and the probe nucleic acid molecule comprises a sequence as set forth in SEQ ID NO.:27.

In further embodiments, the instant disclosure provides a composition comprising nucleic acid molecules specific for HLA-DRB1*14, wherein the forward nucleic acid molecule comprises a sequence as set forth in SEQ ID NO.:31, the reverse nucleic acid molecule comprises a sequence as set forth in SEQ ID NO.:32, and the probe nucleic acid molecule comprises a sequence as set forth in SEQ ID NO.:33.

In further embodiments, the instant disclosure provides a composition comprising nucleic acid molecules specific for HLA-DRB4, wherein the forward nucleic acid molecule comprises a sequence as set forth in SEQ ID NO.:34, the reverse nucleic acid molecule comprises a sequence as set forth in SEQ ID NO.:35, and the probe nucleic acid molecule comprises a sequence as set forth in SEQ ID NO.:36.

In further embodiments, the instant disclosure provides a composition comprising nucleic acid molecules specific for HLA-DQA1*01, wherein the forward nucleic acid molecule comprises a sequence as set forth in SEQ ID NO.:37, the reverse nucleic acid molecule comprises a sequence as set forth in SEQ ID NO.:38, and the probe nucleic acid molecule comprises a sequence as set forth in SEQ ID NO.:39.

In further embodiments, the instant disclosure provides a composition comprising nucleic acid molecules specific for HLA-DQA1*03, wherein the forward nucleic acid molecule comprises a sequence as set forth in SEQ ID NO.:40, the reverse nucleic acid molecule comprises a sequence as set forth in SEQ ID NO.:41, and the probe nucleic acid molecule comprises a sequence as set forth in SEQ ID NO.:42.

In further embodiments, the instant disclosure provides a composition comprising comprises nucleic acid molecules specific for HLA-DQA1*05, wherein the forward nucleic acid molecule comprises a sequence as set forth in SEQ ID NO.:43, the reverse nucleic acid molecule comprises a sequence as set forth in SEQ ID NO.:44, and the probe nucleic acid molecule comprises a sequence as set forth in SEQ ID NO.:45.

In further embodiments, the instant disclosure provides a composition comprising nucleic acid molecules specific for HLA-DQB1*03, wherein the forward nucleic acid molecule comprises a sequence as set forth in SEQ ID NO.:49, the reverse nucleic acid molecule comprises a sequence as set forth in SEQ ID NO.:50, and the probe nucleic acid molecule comprises a sequence as set forth in SEQ ID NO.:51.

In further embodiments, the instant disclosure provides a composition comprising nucleic acid molecules specific for HLA-DQB1*04, wherein the forward nucleic acid molecule comprises a sequence as set forth in SEQ ID NO.:52, the reverse nucleic acid molecule comprises a sequence as set forth in SEQ ID NO.:53, and the probe nucleic acid molecule comprises a sequence as set forth in SEQ ID NO.:54.

In further embodiments, the instant disclosure provides a composition comprising nucleic acid molecules specific for HLA-DQB1*06, wherein the forward nucleic acid molecule comprises a sequence as set forth in SEQ ID NO.:55, the reverse nucleic acid molecule comprises a sequence as set forth in SEQ ID NO.:56, and the probe nucleic acid molecule comprises a sequence as set forth in SEQ ID NO.:57.

In further embodiments, the instant disclosure provides a composition comprising nucleic acid molecules specific for SE-HR, wherein (a) the forward nucleic acid molecule comprises a sequence as set forth in SEQ ID NO.:58, the reverse nucleic acid molecule comprises a sequence as set forth in SEQ ID NO.:59, and the probe nucleic acid molecule comprises a sequence as set forth in SEQ ID NO.:60, or (b) the forward nucleic acid molecule comprises a sequence as set forth in SEQ ID NO.:61, the reverse nucleic acid molecule comprises a sequence as set forth in SEQ ID NO.:62, and the probe nucleic acid molecule comprises a sequence as set forth in SEQ ID NO.:63. In related embodiments, the aforementioned compositions may further comprise an inhibitor nucleic acid molecule comprising a sequence as set forth in SEQ ID NO.:85.

In further embodiments, the instant disclosure provides a composition comprising nucleic acid molecules specific for SE-LR, wherein the forward nucleic acid molecule comprises a sequence as set forth in SEQ ID NO.:64, the reverse nucleic acid molecule comprises a sequence as set forth in SEQ ID NO.:65, and the probe nucleic acid molecule comprises a sequence as set forth in SEQ ID NO.:66.

In further embodiments, the instant disclosure provides a composition comprising nucleic acid molecules specific for GSTT1, wherein the forward nucleic acid molecule comprises a sequence as set forth in SEQ ID NO.:70, the reverse nucleic acid molecule comprises a sequence as set forth in SEQ ID NO.:71, and the probe nucleic acid molecule comprises a sequence as set forth in SEQ ID NO.:72.

In further embodiments, the instant disclosure provides a composition comprising nucleic acid molecules specific for AT3, wherein (a) the forward nucleic acid molecule comprises a sequence as set forth in SEQ ID NO.:73, the reverse nucleic acid molecule comprises a sequence as set forth in SEQ ID NO.:74, and the probe nucleic acid molecule comprises a sequence as set forth in SEQ ID NO.:75, or (b) the forward nucleic acid molecule comprises a sequence as set forth in SEQ ID NO.:76, the reverse nucleic acid molecule comprises a sequence as set forth in SEQ ID NO.:77, and the probe nucleic acid molecule comprises a sequence as set forth in SEQ ID NO.:78.

In further embodiments, the instant disclosure provides a composition comprising nucleic acid molecules specific for Tg, wherein (a) the forward nucleic acid molecule comprises a sequence as set forth in SEQ ID NO.:79, the reverse nucleic acid molecule comprises a sequence as set forth in SEQ ID NO.:80, and the probe nucleic acid molecule comprises a sequence as set forth in SEQ ID NO.:81, or (b) the forward nucleic acid molecule comprises a sequence as set forth in SEQ ID NO.:82, the reverse nucleic acid molecule comprises a sequence as set forth in SEQ ID NO.:83, and the probe nucleic acid molecule comprises a sequence as set forth in SEQ ID NO.:84.

In any of the aforementioned embodiments, the instant disclosure provides a composition wherein the probe comprises a fluorophore at the 5'-end and a quencher at the 3'-end. In any of the aforementioned embodiments, the instant disclosure provides a composition wherein the fluorophore is FAM and the quencher is TAMRA or BHQ. In any of the aforementioned embodiments, the instant disclosure provides a composition wherein the probe further comprises a duplex stabilizer, such as at least one LNA or MGB.

Although specific embodiments and examples of this disclosure have been described herein for illustrative purposes, various equivalent modifications can be made without departing from the spirit and scope of the invention, as will be recognized by those skilled in the relevant art after reviewing the present disclosure. The various embodiments described can be combined to provide further embodiments. The described devices, systems and methods can omit some elements or acts, can add other elements or acts, or can combine the elements or execute the acts in a different manner or order than that illustrated, to achieve various advantages of the invention. These and other changes can be made to the invention in light of the above detailed description.

In general, in the following claims, the terms used should not be construed to limit the invention to the specific embodiments disclosed in the specification. Accordingly, the invention is not limited by the disclosure, but instead its scope is determined entirely by the following claims

EXAMPLES

Example 1

Measuring Allograft Rejection by HLA-Specific Q-PCR of Transplant Recipient Serum There is no reliable serum marker available to monitor incipient pancreas or islet-cell rejection. Quantification of donor specific genomic DNA in serum was measured as a marker of rejection. A panel of HLA-specific quantitative PCR assays (Q-PCR) was used to test 158 sera from 42 pancreas-kidney transplant recipients. The HLA-specific primers and probes used were directed to DRB1*01 (SEQ ID NOS:4, 5 and 6), DRB1*11 (forward primer CAG ACC ACG TTT CTT GGA GTA CTC TAC, SEQ ID NO.:86; reverse primer CCT TCT GGC TGT TCC AGT ACT CCT, SEQ ID NO.:87, and probe CGC TCC GTC CCA TTG AAG AAA TGA CA, SEQ ID NO.:88), DQA1*01 (SEQ ID NOS:37, 38 and 39), DQA1*03 (SEQ ID NOS:40, 41 and 42), DQB1*02 (SEQ ID NOS:46, 47 and 48), DQB1*03 (SEQ ID NOS:49, 50 and 51), DQB1*06 (SEQ ID NOS:55, 56 and 57), DRB4*01 (SEQ ID NOS:34, 35 and 36), and B*44 (SEQ ID NOS:1, 2 and 3). Temporally related biopsies for 65 sera permitted analysis for correlation of donor DNA concentrations with rejection.

Briefly, a calibration curve for the HLA-specific assay of interest was generated with known quantities of genomic DNA [0, 0.5, 1, 5, 10, 50, 100, and 500 genome-equivalents (gEq)] derived from Epstein-Barr virus—transformed cell lines that were previously HLA typed and known to be homozygous for the allele of interest. A separate β-globin calibration curve was created to quantify the total amount of genomic DNA derived from both host and donor within each specimen. Total genomic DNA was isolated from patient sera (200 to 500 μL) by use of a DNA Mini Kit (Qiagen) with a final elution volume of 50 μL. Specimen HLA Q-PCR reactions contained 10 μL of template DNA (or 5 μL for the β-globin assay to maximize the amount of DNA eluate available for HLA assays), 25 μL of TaqMan® Universal Master Mix (Applied Biosystems), 300 nM each of the forward/reverse primers (MWG Biotech), 100 nM dual labeled probe (MWG Biotech), and DNase/RNase-free water to a final volume of 50 μL. Of note, to prevent PCR competition for the reagents between the more prevalent β-globin PCR product and the less prevalent HLA-specific product, assays were performed in a non-multiplexed format with HLA-specific and β-globin assays contained in separate wells on the same plate. Four wells were measured, on average, for each serum sample for HLA and 1 well for β-globin. PCR reactions were incubated in an ABI Prism 7000 thermocycler for 2 min at 50° C., followed by 45 cycles of 95° C. for 15 s and 60 to 64° C., depending on the HLA assay, for 1 min. HLA (or β-globin) quantities were determined for sample wells by plotting on the calibration curve the point at which a fluorescence threshold for a given assay was exceeded. Results were rejected and assays repeated if either calibration curve correlation coefficient (r2) was <0.99.

HLA quantities were expressed as the total number of cell-free gEq/mL of serum as calculated by the equation: ΣHLA Values/Σ Sample Volume×elution volume×1000/serum volume=gEq/mL. The equation accounts for the proportion of the DNA extract that was amplified for each target allele (elution volume/sum of sample volume). In addition, we determined the ratio of donor DNA to host cell-free DNA (as determined by simultaneous β-globin Q-PCR) in the serum to control for nonspecific increases in total soluble DNA. The ratio was subsequently corrected to reflect whether the assayed HLA allele was present in 1 or 2 copies in the donor genome.

Results: Donor DNA concentrations were higher in sera from recipients who had experienced allograft rejection (n=31) than from those who had not (n=34). Median concentrations, expressed as the genome-equivalent (gEq) number of donor cells per $10^6$ host cells, were 2613 and 59 gEq/$10^6$, respectively (P=0.03). Relative concentrations of donor DNA in host serum (gEq/106 host genomes) over time for an exemplary patient probed with DQB1*06 is shown in FIG. 1.

Conclusion: Q-PCR for donor-specific genetic polymorphisms is a noninvasive approach to monitor pancreas-kidney, as well as other types of allograft rejection.

Example 2

Measuring Maternal Microchimerism by HLA-Specific Q-PCR

Microchimerism (Mc), originating from bidirectional fetal-maternal cell traffic during pregnancy has been identified in healthy adults and in patients with scleroderma (systemic sclerosis, "SSc"). HLA-specific primers and fluorogenic probes were used in real-time quantitative polymerase chain reaction assays to investigate the frequency and quantitative levels of maternal Mc ("MMc") in healthy women and women with SSc.

Briefly, HLA-specific primers and probes were used to target non-inherited, non-shared HLA sequences. DNA-based HLA typing was conducted in 67 proband mother pairs and in all children if the proband was parous. Statistical analysis was limited to 50 proband mother pairs (including 32 healthy women and 18 women with SSc) in whom MMc could be distinguished from potential fetal Mc. The probands were either healthy women with no history of autoimmune disease, or women with scleroderma. A total of 253 subjects were studied and included healthy women (n=41) and their mothers (n=41) and children (n=58), and women with SSc (n=26) and their mothers (n=26) and children (n=39). The study population was derived from an overall population of 74 healthy women and 56 women with SSc, among whom 85% had a non-inherited, non-shared maternal HLA-DRB1, DRB3, DRB4, DRB5, DQA1, DQB1, or B allele, with 70% of HLA differences informative using same panel of 8 HLA-specific primers in Q-PCR assays as described in Example 1. Probands who were parous were included in the current study only if all living children were also willing to be studied. This requirement was included because fetal Mc from a prior pregnancy can confound the detection of MMc. Parity was similar in the two groups, and the study subjects were recruited from a similar geographic distribution (state of Washington and surrounding areas). All subjects provided informed consent.

Another potential source of microchimerism is blood transfusion (Lee et al., *Blood* 93:3127, 1999). The HLA primers used in this study are specific for a particular HLA polymorphism, and chances are extremely low that the blood donor had the same HLA allele as the mother of the proband. Of the 32 controls for whom information on blood transfusion history was available, one had had a blood transfusion prior to the study. Of the 25 scleroderma patients, five had had a blood transfusion (one prior to disease onset, one at the time of onset, and three after onset).

Results. MMc in peripheral blood mononuclear cells was more frequent among women with SSc (72%) than healthy women (22%) (odds ratio: women with SSc were 9.3 times more likely to have MMc than healthy women, P<0.001) (see Table 2).

TABLE 2

Frequency of MMc in Healthy Women and Women with SSc*

|  | No. (%) Positive | Odds Ratio | 95% CI | P vs. Controls |
|---|---|---|---|---|
| Model with all Probands |  |  |  |  |
| Controls | 7/32 (21.9) | 9.3 | 2.5-35 | 0.001 |
| Cases | 13/18 (72.2) |  |  |  |
| Model excluding Probands with transfusions |  |  |  |  |
| Controls | 7/31 (22.6) | 6.2 | 1.6-25 | 0.01 |
| Cases | 9/14 (64.3) |  |  |  |

*MMc = maternal microchimerism;
SSc = systemic sclerosis;
95% CI = 95% confidence interval.

However, levels of MMc, expressed as the genome equivalent of maternal cells per million (gEq/mil), were not significantly different (0-68.6 gEq/mil in SSc patients, 0-54.5 in healthy women) (see Table 3).

TABLE 3

Frequency of MMc in Healthy Women and Women with SSc*

|  | No. of Subjects/ Observations | gEq/mil host cells, median (range) | P vs. Controls |
|---|---|---|---|
| Model with all Probands |  |  |  |
| Controls | 32/34 | 0 (0-54.5) | 0.056 |
| Cases | 18/24 | 0.71 (0-68.6) |  |
| Model excluding Probands with transfusions |  |  |  |
| Controls | 31/33 | 0 (0-54.5) | 0.18 |
| Cases | 14/20 | 0.71 (0-34.5) |  |

*MMc = maternal microchimerism;
SSc = systemic sclerosis;
gEq/mil = genome equivalent per million.

Figure 2:
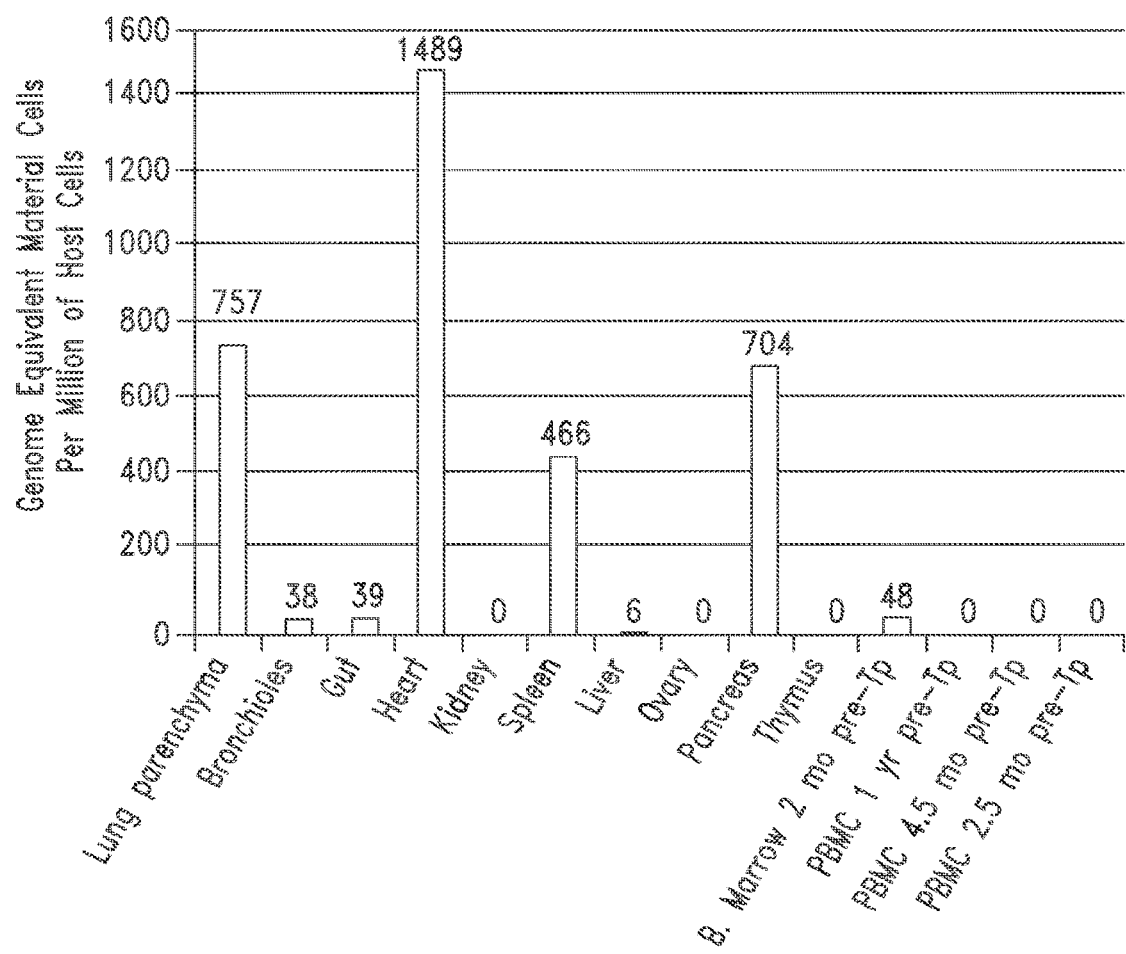
FIG. 2 shows a bar graph illustrating quantitative expression of maternal microchimerism in different tissues, peripheral blood mononuclear cells (PBMCs), and bone marrow (B. marrow) from a proband with systemic sclerosis. Tp=autologous hematopoietic stem cell transplantation.

In additional studies, positivity for MMc was demonstrated in a bone marrow aspirate from an SSc patient in whom peripheral blood had been found to be negative for MMc on four occasions, and tissue from a subsequent autopsy of this patient had MMc levels of 757 and 1,489 gEq/mil in the lung and heart, respectively (see FIG. 2).

Conclusion. MMc is not uncommon in the peripheral blood of healthy adults, is increased in frequency in patients with SSc, and may be present in bone marrow and disease-affected tissues even if absent in the peripheral blood.

What is claimed is:

1. A composition, comprising a forward nucleic acid molecule, a reverse nucleic acid molecule, and a probe nucleic acid molecule, wherein the forward, reverse and probe nucleic acid molecules are complementary to SE-LR (DERAA (SEQ ID NO:89)), and wherein the forward nucleic acid molecule has a length of up to 23 nucleotides and comprises the sequence as set forth in SEQ ID NO.:64, the reverse nucleic acid molecule has a length of up to 26 nucleotides and comprises the sequence as set forth in SEQ ID NO.:65, and the probe nucleic acid molecule comprises a nucleic acid sequence, a fluorophore and a quencher, wherein the nucleic acid sequence has a length of up to 18 nucleotides and comprises the sequence as set forth in SEQ ID NO.:66.

2. The composition according to claim 1, wherein the fluorophore is located at the 5'-end of the probe nucleic acid molecule and the quencher is located at the 3'-end of the probe nucleic acid molecule.

3. The composition of claim 2, wherein the fluorophore is FAM and the quencher is TAMRA or BHQ.

4. The composition of claim 2, wherein at least one nucleotide of the probe is a duplex stabilizer.

5. The composition of claim 4, wherein the duplex stabilizer is at least one LNA or MGB.

6. A kit comprising a nucleic acid composition according to claim 1.

7. The kit of claim 6, further comprising one or more reagents for performing PCR.

8. A process for detecting microchimerism, comprising:
   (a) amplifying target nucleic acid molecules of a test biological sample using one or more nucleic acid compositions according to claim 1, wherein the test biological sample comprises a known HLA genotype;
   (b) amplifying nucleic acid molecules of a control biological sample using the one or more nucleic acid molecule compositions of (a), wherein the control biological sample comprises a known HLA genotype that is different from the test biological sample; and
   (c) detecting the presence of microchimerism when the amplification from the test biological sample and the control biological sample identifies HLA markers in the test biological sample that are also present in the control biological sample.

9. The process of claim 8, wherein the detection sensitivity is one chimeric genome in $10^5$ host genomes.

10. The process of claim 8, wherein the test biological sample is blood or serum.

11. The process of claim 8, wherein the microchimerism detected is maternal microchimerism.

12. The process of claim 8, wherein the microchimerism detected is fetal microchimerism.

13. The process of claim 8, wherein amplifying comprises performing Q-PCR.

14. A method for detecting incipient allograft rejection, comprising:
   (a) obtaining a first biological sample from a subject prior to receiving a transplant from a transplant donor and a second biological sample from the same subject after receiving the transplant during a period of time when there is a risk of rejection;
   (b) amplifying target nucleic acid molecules from the first and second biological samples using one or more nucleic acid compositions according to claim 1, wherein one or more of the nucleic acid compositions comprising the forward, the reverse, and the probe nucleic acid molecules are complementary to target nucleic acid molecules found in the transplant donor and not found in the transplant recipient; and
   (c) detecting incipient allograft rejection in the transplant recipient when the presence of amplified target nucleic acid molecules from the transplant donor are detected in the transplant recipient.

15. The method of claim 14, wherein the first biological sample and/or the second biological sample is blood or serum.

16. The method of claim 14, wherein the transplant comprises a kidney transplant, a pancreas transplant, an islet cell transplant, a hematopoietic cell transplant, a cord blood transplant or a bone marrow transplant.

17. The method of claim 14, wherein the subject is human.

18. The method of claim 14, wherein the subject has a known genotype.

19. The method of claim 14, wherein amplifying comprises performing Q-PCR.

* * * * *